US00PP30331P2

(12) United States Plant Patent
Ronald et al.

(10) Patent No.: US PP30,331 P2
(45) Date of Patent: Apr. 2, 2019

(54) ***SYRINGA* PLANT NAMED 'JEFLADY'**

(50) Latin Name: *Syringa meyeri x Syringa patula*
Varietal Denomination: Jeflady

(71) Applicant: Jeffries Nurseries Ltd, Portage la Prairie (CA)

(72) Inventors: Wilbert Ronald, Portage la Prairie (CA); Rick Durand, West Kelowna (CA)

(73) Assignee: JEFFRIES NURSERIES LTD, Portage la Prairie, MB (CA)

( * ) Notice: Subject to any disclaimer, the term of this patent is extended or adjusted under 35 U.S.C. 154(b) by 0 days.

(21) Appl. No.: 15/731,354

(22) Filed: Jun. 1, 2017

(51) Int. Cl.
*A01H 5/02* (2018.01)

(52) U.S. Cl.
USPC ..... Plt./248

(58) Field of Classification Search
USPC ..... Plt./248
See application file for complete search history.

*Primary Examiner* — Keith O. Robinson
(74) *Attorney, Agent, or Firm* — Penny J. Aguirre

(57) ABSTRACT

A new cultivar of *Syringa* hybrid plant named 'Jeflady' that is characterized by its compact and dense plant habit, its numerous panicles that are large in size, its fragrant, full panicles with purple flower buds opening to lilac pink flowers, its leaves that are elliptic in shape with impressed veins and margins that are only slightly undulated.

2 Drawing Sheets

Botanical classification: *Syringa meyeri* x *Syringa patula*.
Variety denomination: 'Jeflady'.

BACKGROUND OF THE INVENTION

The present invention relates to a new and distinct cultivar of *Syringa* of hybrid origin that is botanically known as *Syringa* 'Jeflady' and will be referred to hereafter by its cultivar name, 'Jeflady'. 'Jeflady' is a new cultivar of lilac grown for use as an ornamental landscape plant.

'Jeflady' arose from an on going breeding program conducted by the Inventors in Portage la Prairie, Manitoba, Canada. The objectives of the breeding program are to develop new cultivars of *Syringa* with a compact and dwarf plant habiat, improved flowering and hardiness under prairie conditions.

'Jeflady' originated as a cross made by the Inventors in 2004 between *Syringa meyeri* 'Palibin' (not patented) as the female parent and *Syringa patula* 'Miss Kim' (not patented) as the male parent. The Inventors selected 'Jeflady' as a single unique plant amongst the seedlings that resulted from the above cross in 2008.

Asexual propagation of the new cultivar was first accomplished by stem cuttings in June 2011 under the direction of the Inventors in Glenlea, Manitoba, Canada. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Jeflady' as a unique cultivar of *Syringa*.

1. 'Jeflady' exhibits a compact and dense plant habit.
2. 'Jeflady' exhibits numerous panicles that are large in size.

3. 'Jeflady' exhibits leaves that are elliptic in shape with impressed veins.
4. 'Jeflady' exhibits fragrant, full panicles with purple flower buds opening to lilac pink flowers.
5. 'Jeflady' exhibits leaf margins that only slightly undulated.

The female parent of 'Jeflady', 'Palibin', differs from 'Jeflady' in having leaves that are smaller in size, flowers that are white-pink in color, panicles that are smaller in size and that lack fall foliage color. The male parent of 'Jeflady', 'Miss Kim', differs from 'Jeflady' in having a larger plant size, leaves that are smaller in size, flowers that are lavender-blue in color, and purple fall foliage. The new *Syringa* can be most closely compared to *Syringa* cultivars 'Pink Perfume' (U.S. Plant Pat. No. 24,252) and 'Penda' (U.S. Plant Pat. No. 20,575). 'Pink Perfume' and 'Penda' are both similar to 'Jeflady' in having compact plant habits and fragrant flowers. 'Pink Perfume' differs from 'Jeflady' in having flowers that are pink in color, a repeat blooming habit and leaves that are smaller in size. 'Penda' differs from 'Jeflady' in having flowers that are purple in color, a repeat blooming habit and leaves that are smaller in size.

BRIEF DESCRIPTION OF THE DRAWINGS

The accompanying colored photographs illustrate the overall appearance and distinct characteristics of the new *Syringa*. The photographs were taken of 3 year-old plants as grown outdoors in two-gallon containers at a nursery in Portage la Prairie, Manitoba, Canada.

The photograph in FIG. 1 provides a side view of a plant of 'Jeflady' in bloom.

Figure 1:
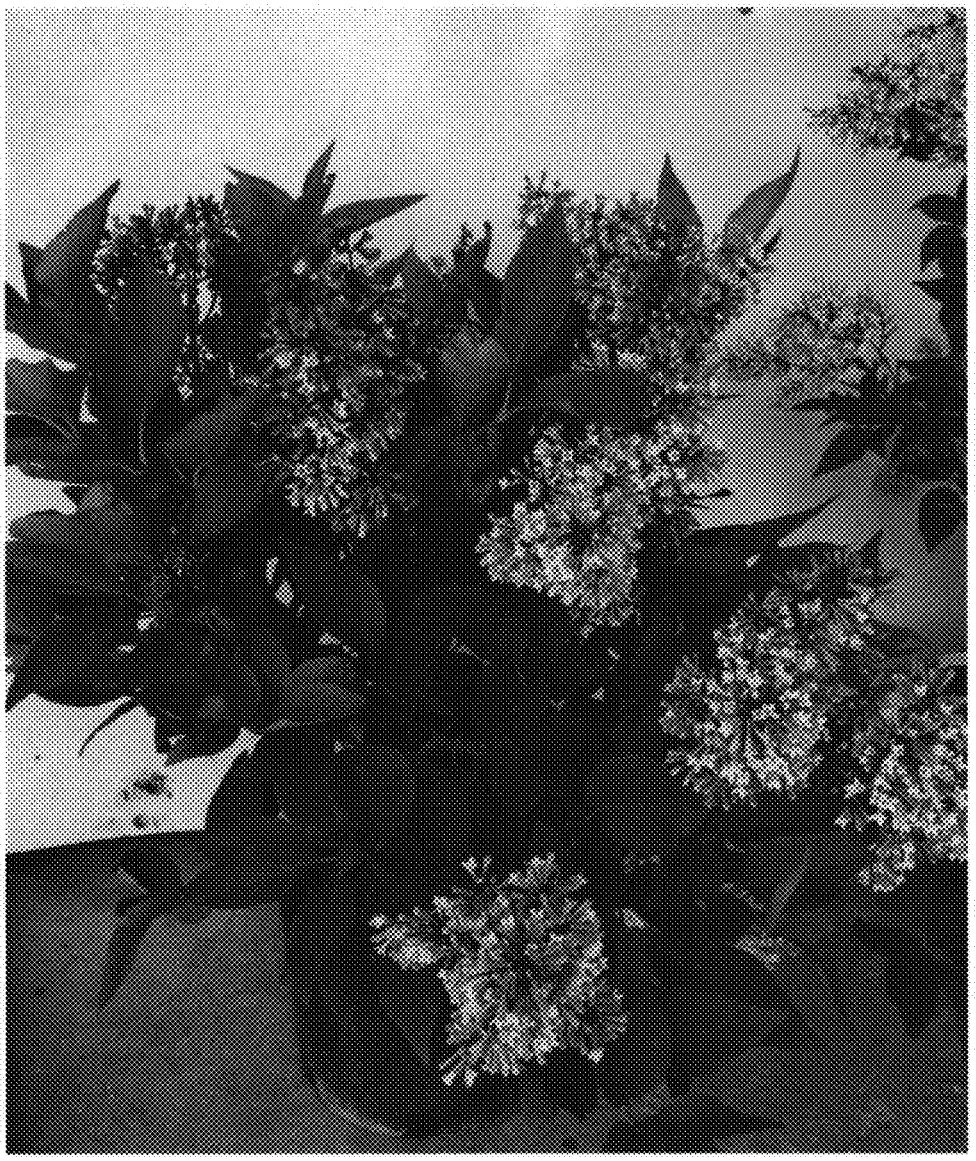
Figure 2:
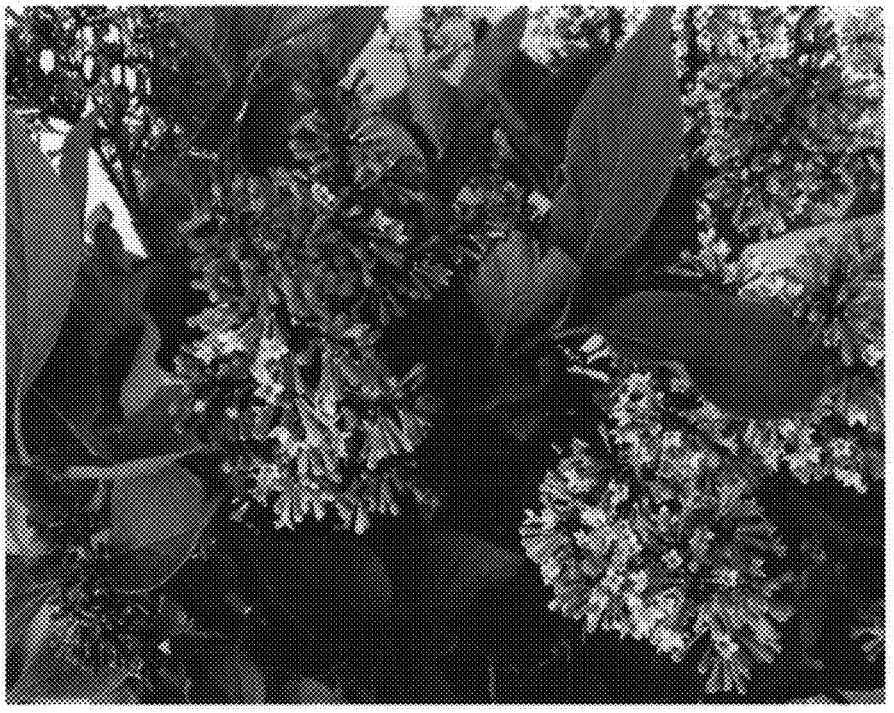

The photograph in FIG. 2 provides a close-up view of the inflorescences of 'Jeflady'.

Figure 3:
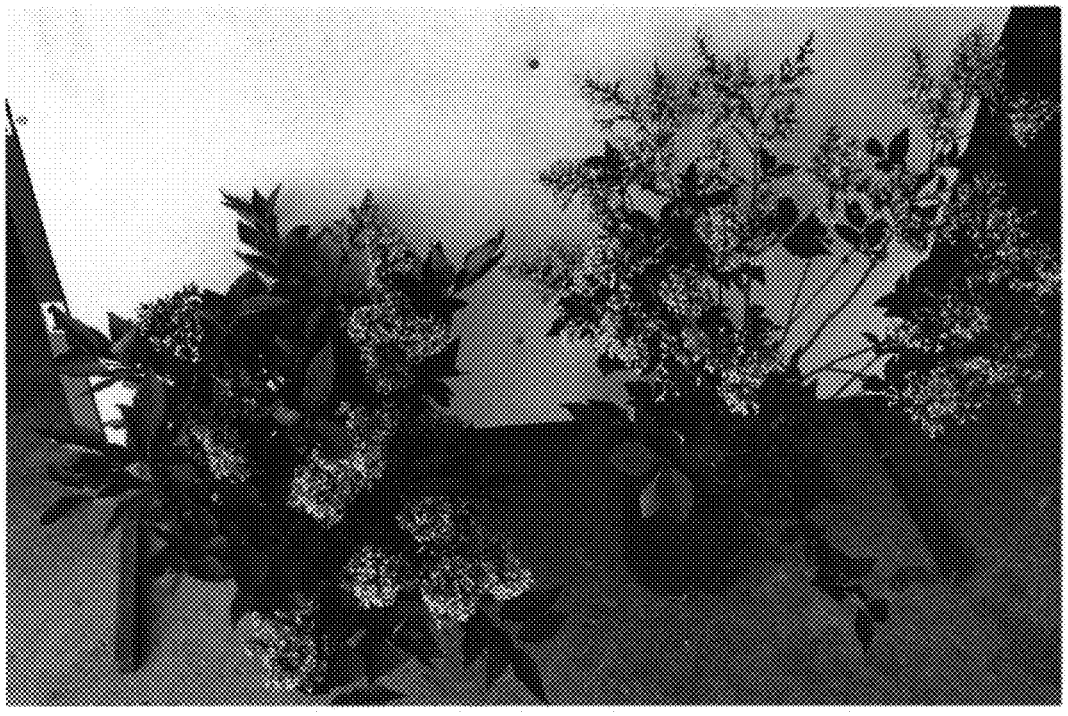

The photograph in FIG. 3 provides a comparison of 'Jeflady' on the left and 'Miss Kim' on the right.

The colors in the photographs are as close as possible with the photographic and printing technology utilized and the color values cited in the detailed botanical description accurately describe the colors of the new *Syringa*.

DETAILED BOTANICAL DESCRIPTION

The following is a description of 1.5 year-old plants as grown outdoors in one-gallon containers in Portage la Prairie, Manitoba, Canada. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—10 days in the first half of June in Canada.

*Plant type*.—Deciduous shrub.

*Plant habit*.—Compact, dense.

*Height and spread*.—An average of 1.25 m in height and width when mature in the landscape.

*Hardiness*.—At least in U.S.D.A. Zone 2.

*Diseases*.—No resistance or susceptibility to diseases has been observed.

*Root description*.—Fibrous and dense, a blend of 165A and 161D in color.

*Propagation*.—Stem cuttings.

*Growth rate*.—Moderate.

*Root development*.—Softwood cuttings root readily in 6 weeks in a hot house under intermittent mist, rooted cuttings are easily overwintered and roots will fully develop in a one-quart container by mid-summer the following year.

Branch description:

*Branch shape*.—Rounded.

*Branch color*.—Young; 143B, mature branches and trunk; 198A.

*Branch size*.—Young lateral branches; 11 cm in length, 2 mm in diameter, mature branches; 5 cm in length, 3 mm in width, trunk; 4 cm in length, 5 mm in diameter at the soil line.

*Branch surface*.—Young branches; smooth and glabrous, moderately covered with lenticels, an average of 15 lenticels per cubic cm, 155A and light flushes of 166B around the lenticels, mature branches and trunk; slightly rugose, dull and bark-like, moderately covered with lenticels, an average of 15 lenticels per cubic cm, 155A in color and an average of 0.5 mm in diameter.

*Branch quantity*.—Average of 2 main branches, average of 5 mature branches per main branches, average of 4 young lateral branches growing per mature branch.

*Internode length*.—Up to 2.5 cm.

*Branching*.—Held upright to slightly drooping.

Foliage description:

*Leaf shape*.—Elliptic.

*Leaf division*.—Simple.

*Leaf base*.—Acute.

*Leaf apex*.—Acuminate.

*Leaf fragrance*.—None.

*Leaf venation*.—Pinnate, upper surface color; matches leaf color and slighty transluscent, lower surface color; matches leaf color, main vein is 145B in color, slighty transluscent.

*Leaf margins*.—Entire and slightly undulate, densely covered with pubescent stiff hairs that match the leaf color.

*Leaf arrangement*.—Opposite.

*Leaf attachment*.—Petiolate.

*Leaf surface*.—Both surfaces are gloubrous and slightly shiny to matte.

*Leaf size*.—An average of 7.5 cm in length and 3 cm in width.

*Leaf quantity*.—An average of 20 leaves per mature branch.

*Leaf color*.—Young and mature leaves upper surface; 137B; young and mature leaves lower surface; 147C, both surfaces become suffused with a blend of 183A and 187A in fall.

*Petioles*.—An average of 2 cm in length and 1 mm in width, surface glabrous, 145A in color.

*Bracts*.—An average of 2, at the base of a leaf cluster, an average of 5 mm in length and 2 mm in width, upper and lower surfaces; dull and glabrous and 137B in color.

Inflorescence description:

*Inflorescence type*.—Thyrse compound panicles on terminals and laterals, broad ovate in overall shape.

*Inflorescence size*.—An average of 12 cm in length and 8 cm in width.

*Attitude of inflorescence*.—Upright to semi-upright.

*Rachis*.—Rounded in shape, up to 10 cm in length and an average of 1 mm in width, surface is glabrous, moderately strong, color is mostly N187 with flushes of 138A, tiny lenticels densely cover the surface, average of <0.5 mm in length and 164B in color.

*Peduncles*.—An average of 6 cm in length and 2 mm in width, glabrous and shiny surface, moderate strength, 138B with a very slight flush of 178A, tiny lenticels densely cover the surface, average of <0.5 mm in length and 164B in color.

*Flower buds*.—Spatulate in shape, an average of 1 cm in length and 2 mm diameter at the apex tapering to 1 mm at the base, color; young newly developed buds are 77A, maturing buds flushed with 77A and 76A, blending to NN155D at base.

*Flower fragrance*.—Sweet, strong, lilac scent.

*Persistence of flowers*.—Self-cleaning, calyx persistent.

*Lastingness of flowers*.—Individual panicles bloom for about 2 weeks, depending on temperature.

*Flower quantity*.—An average of 180 flowers per compound panicle.

*Flower type*.—Salverform with spreading petals.

*Flower aspect*.—Upwards and outward.

*Flower size*.—An average of 1.5 cm in length and 6 mm at apex, tapering to 1 mm at the base.

*Petals*.—4, free petal lobes; an average of 3 mm in length and 2 mm in width, oblong in shape with acute apices, entire margin, lower 80% fused forming a narrow tube, upper and lower surfaces smooth and glabrous, color; when opening inner and outer surface 69D with a range of very light flushes of 76C and 77B, when fully open inner and outer surface NN155D, undulation absent, incurving of the margin absent, attitude semi-erect with apex slightly recurved.

*Flower tube.*—1.2 cm in length and 2 mm in width, inner and outer surfaces are smooth and globrous, color; when opening inner and outer surface 69D with a range of very light flushes of 76C and 77B, when fully open inner and outer surface 76D.

*Calyx.*—Campanulate, about 1.5 mm in depth and 1 mm in width, comprised of 4 fused sepals with tips unfused with acute apexes, glabrous inner and outer surface, young; 144A in color, mature; N77A.

Reproductive organs:

*Pistils.*—1, inserted deep into calyx, average of 3 mm in length, stigma; minute in size, oval in shape, NN155D in color, style; NN155D in color.

*Stamens.*—2, extend beyond corolla, anthers; an average of 2 mm in length and 165A in color, filaments; about 7 mm in length and NN155D in color, pollen; abundant in quantity and 158A in color.

*Fruit and seed.*—No seed or fruit produced.

It is claimed:

1. A new and distinct cultivar of *Syringa* plant named 'Jeflady' as herein illustrated and described.

* * * * *